United States Patent
Kraatz et al.

(10) Patent No.: US 6,908,937 B2
(45) Date of Patent: Jun. 21, 2005

(54) HETEROCYCLIC FLUOROALKENYL THIOETHERS (II)

(75) Inventors: Udo Kraatz, Leverkusen (DE); Bernd Gallenkamp, Wippertal (DE); Albrecht Marhold, Leverkusen (DE); Peter Wolfrum, Monheim (DE); Wolfram Andersch, Bergisch Gladbach (DE); Christoph Erdelen, Leichlingen (DE); Andreas Turberg, Leverkusen (DE); Olaf Hansen, Langenfeld (DE); Achim Harder, Köln (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 10/332,635

(22) PCT Filed: Jul. 2, 2001

(86) PCT No.: PCT/EP01/07521

§ 371 (c)(1),
(2), (4) Date: May 6, 2003

(87) PCT Pub. No.: WO02/06256

PCT Pub. Date: Jan. 24, 2002

(65) Prior Publication Data

US 2003/0207869 A1 Nov. 6, 2003

(30) Foreign Application Priority Data

Jul. 13, 2000 (DE) .......................... 100 34 131

(51) Int. Cl.$^7$ ..................... C07D 271/10; A01N 43/836
(52) U.S. Cl. ..................... 514/363; 544/53; 548/136; 548/142; 548/144
(58) Field of Search .................... 544/53; 548/136, 548/142, 144; 514/363

(56) References Cited

U.S. PATENT DOCUMENTS

| | | | | |
|---|---|---|---|---|
| 3,914,251 A | | 10/1975 | Brokke ................. | 260/326 NS |
| 5,026,460 A | | 6/1991 | Dapperheld ............. | 204/59 R |
| 5,705,516 A | * | 1/1998 | Turnbull et al. ........... | 514/380 |
| 5,728,833 A | | 3/1998 | Turnbull et al. ........... | 544/309 |
| 5,914,423 A | | 6/1999 | Turnbull et al. ............. | 558/54 |

FOREIGN PATENT DOCUMENTS

| | | |
|---|---|---|
| EP | 0 217 747 | 4/1987 |
| JP | 11-140063 | 5/1999 |
| WO | 94/06777 | 3/1994 |
| WO | 94/29268 | 12/1994 |
| WO | 95/24403 | 9/1995 |
| WO | 99/52874 | 10/1999 |
| WO | 99/52882 | 10/1999 |

OTHER PUBLICATIONS

Helvetica Chimica Acta—vol. 55, Fasc. 4, (month unavailable) 1972—Nr. 119–120, pp. 1178–1186, "120 Arbeiten über Phosphorsäure– und Thiophosphorsäureeseter mit einem heterocyclischen Methylübertragung" by K. Rüfenacht.

J. Chem. Soc., Perkin Trans. 2, (month unavailable) 1998, pp. 219–231, "Cyclization reactivities of fluorinated hex–50–enyl radicals" by W. R. Dolbier, Jr. et al.

Pestic. Sci., (month unavailable) 1996, 48, pp. 343–349, "Anthelmintic Actions of the Cyclic Depsipeptide PF1022A and its Electrophysiological Effects on Muscle Cells of *Asaris suum*" by Richard. J. Martin et al.

Tetrahedron Letters, vol. 37, No. 3, pp. 5321–5324, (month unavailable) 1996, "The Kinetic Impact of Vinylic Fluorine Substituents on 5–Hexenyl Radical Cyclizations" by W. R. Dolbier, Jr. and Xiao X. Rong.

* cited by examiner

Primary Examiner—Kamal Saeed
(74) Attorney, Agent, or Firm—Richard E. L. Henderson

(57) ABSTRACT

The present invention relates to novel heterocyclic fluoroalkenyl thioethers of the formula (I)

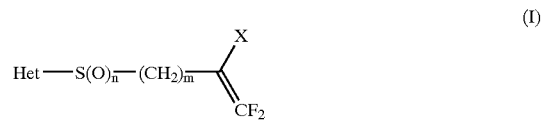

in which
X represents hydrogen, halogen or alkyl,
m represents integers from 3 to 10,
n represents 0, 1 or 2,
Het represents the groups

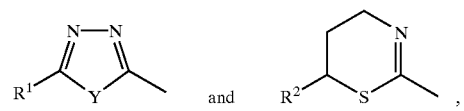

where
$R^1$ represents hydrogen; mercapto; optionally halogen-substituted alkyl, alkoxy, alkylthio, alkylsulphinyl, alkylsulphonyl or alkenyl; optionally substituted aryl; or optionally substituted heterocyclyl,
Y represents oxygen or sulphur, and
$R^2$ represents hydrogen, alkyl or optionally substituted aryl,
and to processes for their preparation and to their use as pesticides.

10 Claims, No Drawings

HETEROCYCLIC FLUOROALKENYL THIOETHERS (II)

The present invention relates to novel heterocyclic fluoroalkenyl thioethers, to processes for their preparation and to their use as pesticides.

It is known that certain heterocyclic fluoroalkenyl thioethers have insecticidal, acaricidal and/or nematicidal properties (cf., for example, U.S. Pat. No. 3,914,251, U.S. Pat. No. 5,952,359, WO 99/52874, WO 99/52882 or JP 11140063). However, in particular at low application rates and concentrations of active compound, the efficacy and/or activity spectrum of these compounds is not always entirely satisfactory.

This invention provides novel heterocyclic fluoroalkenyl thioethers of the formula (I)

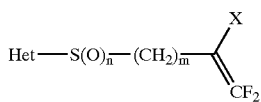
(I)

in which
X represents hydrogen, halogen or alkyl,
m represents integers from 3 to 10,
n represents 0, 1 or 2,
Het represents the groupings

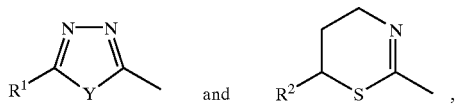

where
$R^1$ represents hydrogen, mercapto, represents in each case optionally halogen-substituted alkyl, alkoxy, alkylthio, alkylsulphinyl, alkylsulphonyl, alkenyl, alkenylthio, alkenylsulphinyl or alkenylsulphonyl, represents optionally substituted aryl or represents optionally substituted heterocyclyl,
Y represents oxygen or sulphur and
$R^2$ represents hydrogen, alkyl or optionally substituted aryl.

Furthermore, it has been found that the heterocyclic fluoroalkenyl thioethers of the formula (I) are obtained when
a) mercapto derivatives of the formula (II)

 (II)

in which
Het is as defined above
are reacted with fluoroalkenyl halides of the formula (III)

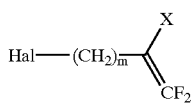
(III)

in which
X and m are each as defined above and
Hal represents halogen, preferably bromine or chlorine, in the presence of a diluent and if appropriate in the presence of a basic reaction auxiliary, where it is also possible to use the compounds of the formula (II) in the form of their salts, preferably the alkali metal salts, such as, in particular, the sodium or potassium salts; and, if appropriate,
b) the resulting heterocyclic fluoroalkenyl thioethers of the formula (IA) according to the invention

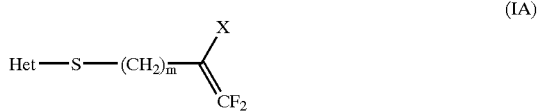
(IA)

in which
Het, X and m are each as defined above
are oxidized with an oxidizing agent, if appropriate in the presence of a diluent and if appropriate in the presence of a catalyst.

Finally, it has been found that the novel heterocyclic fluoroalkenyl thioethers of the formula (I) have highly pronounced biological properties and are suitable especially for controlling animal pests, in particular insects, arachnids and nematodes, encountered in agriculture, in forests, in the protection of stored products and materials and in the hygiene sector.

The formula (I) provides a general definition of the heterocyclic fluoroalkenyl thioethers according to the invention.

Preferred substituents or ranges of the radicals listed in the formulae mentioned above and below are illustrated below:
X preferably represents hydrogen, fluorine, chlorine, bromine or $C_1$–$C_4$-alkyl.
m preferably represents integers from 3 to 8.
n preferably represents 0 or 2.
Het preferably represents the groupings.

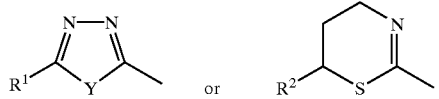

where
$R^1$ represents hydrogen or mercapto, represents $C_1$–$C_8$-alkyl, $C_1$–$C_8$-alkoxy, $C_1$–$C_8$-alkylthio, $C_1$–$C_8$-alkylsulphinyl, $C_1$–$C_8$-alkylsulphonyl, $C_2$–$C_8$-alkenyl, $C_2$–$C_8$-alkenylthio, $C_2$–$C_8$-alkenylsulphinyl or $C_2$–$C_8$-alkenylsulphonyl, each of which is optionally mono- or polysubstituted by identical or different halogens, represents phenyl which is optionally mono- to pentasubstituted by identical or different substituents from the group consisting of halogen, nitro, cyano, thiocyanato, and $C_1$–$C_4$-alkyl, $C_1$–$C_4$-alkoxy or $C_1$–$C_4$-alkylthio, each of which is optionally mono- or polysubstituted by identical or different halogens, or represents 5- or 6-membered heterocyclyl having 1 to 3 N, O or S heteroatoms, which is optionally mono- to pentasubstituted by identical or different substituents from the group consisting of halogen, nitro, cyano, thiocyanato, and $C_1$–$C_4$-alkyl, $C_1$–$C_4$-alkoxy or $C_1$–$C_4$-alkylthio, each of which is optionally mono- or polysubstituted by identical or different halogens.
Y preferably represents oxygen or sulphur, and
$R^2$ represents hydrogen or $C_1$–$C_4$-alkyl.

X particularly preferably represents hydrogen or fluorine.
m particularly preferably represents integers from 3 to 6.
n particularly preferably represents 0.
Het particularly preferably represents the groupings

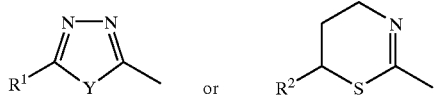

where
R¹ represents hydrogen or mercapto, represents $C_1$–$C_6$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_2$–$C_6$-alkenyl, $C_2$–$C_6$-alkenylthio, $C_2$–$C_6$-alkenylsulphinyl or $C_2$–$C_6$-alkenylsulphonyl, each of which is optionally mono- to pentasubstituted by identical or different substituents from the group consisting of fluorine and chlorine, represents phenyl which is optionally mono- to trisubstituted by identical or different substituents from the group consisting of fluorine, chlorine, bromine, nitro, cyano, thiocyanato, and $C_1$–$C_4$-alkyl, $C_1$–$C_4$-alkoxy or $C_1$–$C_4$-alkylthio, each of which is optionally mono- to pentasubstituted by identical or different substitutents from the group consisting of fluorine and chlorine, or represents furyl, thienyl, pyrazolyl, pyridinyl or pyrimidinyl, each of which is optionally mono- to trisubstituted by identical or different substituents from the group consisting of fluorine, chlorine, bromine, nitro, cyano, thiocyanato, and $C_1$–$C_4$-alkyl, $C_1$–$C_4$-alkoxy or $C_1$–$C_4$-alkylthio, each of which is optionally mono- to pentasubstituted by identical or different substituents from the group consisting of fluorine and chlorine.
Y represents oxygen or sulphur, and
R² represents hydrogen or $C_1$–$C_4$-alkyl.
m very particularly preferably represents 4.
Het very particularly preferably represents the groupings

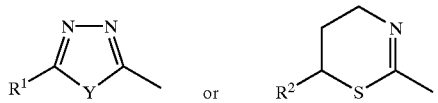

where
R¹ represents hydrogen or mercapto, represents methyl, ethyl, n- or i-propyl, n-, i-, s-, or t-butyl, n-, i- or neo-pentyl, methoxy, ethoxy, n- or i-propoxy, n-, i-, s- or t-butoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, each of which is optionally mono- to pentasubstituted by identical or different substituents from the group consisting of fluorine and chlorine, represents ethenyl, propenyl, butenyl, pentenyl or hexenyl, represents ethenylthio, propenylthio, butenylthio, pentenylthio or hexenylthio, represents ethylsulphinyl, propenylsulphinyl, butenylsulphinyl, pentenylsulphinyl or hexenylsulphinyl, represents ethenylsulphonyl, propenylsulphonyl, butenylsulphonyl, pentenylsulphonyl or hexenylsulphonyl, represents phenyl which is optionally mono- or disubstituted by identical or different substituents from the group consisting of fluorine, chlorine, nitro, cyano, thiocyanato, and methyl, ethyl, methoxy, ethoxy, methylthio and ethylthio, each of which is optionally mono- to pentasubstituted by identical or different substituents from the group consisting of fluorine and chlorine, or represents thienyl or pyridinyl, each of which is optionally mono- or disubstituted by identical or different substituents from the group consisting of fluorine, chlorine, nitro, cyano, thiocyanato, and methyl, ethyl, methoxy, ethoxy, methylthio and ethylthio, each of which is optionally mono- to pentasubstituted by identical or different substituents from the group consisting of fluorine and chlorine,
Y represents oxygen or sulphur, and
R² represents hydrogen, methyl, ethyl, n- or i-propyl.
Het most preferably represents the grouping

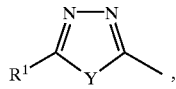

where
R¹ and Y have one of the meanings mentioned above as being preferred, particularly preferred or very particularly preferred for R¹ and Y.

The abovementioned general or preferred radical definitions or illustrations apply both to the end products and, correspondingly, to the starting materials and intermediates. These radical definitions can be combined with one another as desired, i.e. including combinations between the respective preferred ranges.

Preference according to the invention is given to the compounds of the formula (I), which contain a combination of the meanings listed above as being preferred (preferable).

Particular preference according to the invention is given to compounds of the formula (I), which contain a combination of the meanings listed above as being particularly preferred.

Very particular preference according to the invention is given to the compounds of the formula (I) which contain a combination of the meanings listed above as being very particularly preferred.

Most preference according to the invention is given to the compounds of the formula (I) which contain a combination of the meanings listed above as being most preferred.

In the radical definitions listed above and below, hydrocarbon radicals, such as alkyl, are in each case straight-chain or branched as far as this is possible—including in combinations with heteroatoms, such as alkoxy.

Using, for example, 2-mercapto-5-(4-trifluoromethylphenyl)-1,3,7-oxadiazole and 6,6,5-trifluorohex-5-enyl bromide as starting materials, the course of the reaction in the process (a) according to the invention can be represented by the following equation:

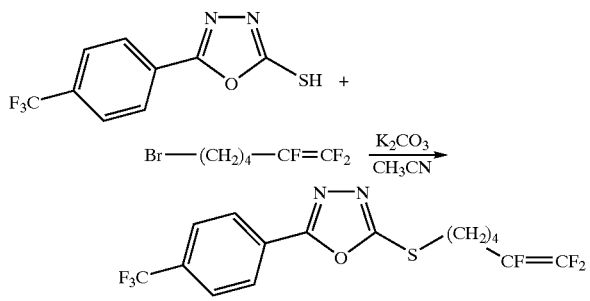

Using, for example, 2-(6,6,5-trifluorohex-5-enylthio)-5-(4-trifluoromethylphenyl)-1,3,4-oxadiazole as starting material and H₂O₂ as oxidizing agent and sodium tungstate as catalyst, the course of the reaction in the process (b) according to the invention can be represented by the following equation:

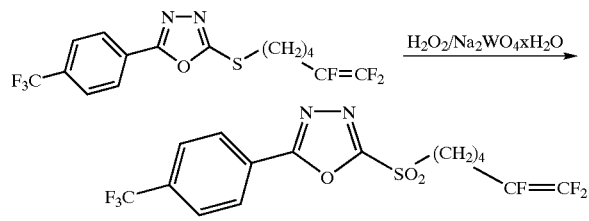

The formula (II) provides a general definition of the mercapto derivatives to be used as starting materials for carrying out process (a) according to the invention.

Most of the mercapto derivatives of the formula (II) are known and/or can be prepared similarly to known processes (cf., for example, Houben-Weyl, Methoden der organischen Chemie [Methods of Organic Chemistry], volume III/part 3, p. 526ff. and/or volume III/part 4, p.189ff., Georg Thieme Verlag Stuttgart 1994; Helvetia Chim. Acta 55, 1178 (1972) or Monatshefte Chemie 113, 793 (1982)).

The formula (III) provides a general definition of the fluoroalkenyl halides furthermore to be used as starting materials in the process (a) according to the invention.

The fluoroalkenyl halides of the formula (III) are known (cf., for example, J. Chem. Soc. Perkin Trans. 2, 219 (1998); Tetrahedron Lett. 37, 5321 (1996); EP 0 334 796 or WO 95/4727), or they are commercially available.

Suitable diluents for carrying out the process (a) according to the invention are inert organic solvents. These include, in particular, aliphatic, alicyclic or aromatic, optionally halogenated hydrocarbons, such as, for example, benzine, benzene, toluene, xylene, anisole, chlorobenzene, dichlorobenzene, petroleum ether, hexane, cyclohexane, dichloromethane, 1,2-dichloroethane, chloroform, carbon tetrachloride; ethers, such as diethyl ether, dioxane, tetrahydrofuran or ethylene glycol dimethyl ether or ethylene glycol diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric triamide; esters, such as ethyl acetate; sulphoxides, such as dimethyl sulphoxide or sulpholane; but also alcohols, such as methanol, ethanol or isopropanol.

If appropriate, the process (a) according to the invention can be carried out in the presence of a basic reaction auxiliary. Suitable basic reaction auxiliaries are all customary inorganic or organic bases. These include, for example, alkali metal and alkaline earth metal hydroxides, such as sodium hydroxide, potassium hydroxide or calcium hydroxide, alkali metal carbonates or bicarbonates, such as sodium carbonate, potassium carbonate, caesium carbonate or sodium bicarbonate, and also tertiary amines, such as triethylamine, N,N-dimethylaniline, pyridine, N,N-dimethyl-aminopyridine, diazabicyclooctane (DABCO), diazabicyclononene (DBN) or diazabicycloundecene (DBU).

When carrying out the process (a) according to the invention, the reaction temperatures can be varied within a relatively wide range. In general, the process is carried out at temperatures between 0° C. and +200° C., preferably at temperatures between +20° C. and +140° C.

For carrying out the process (a) according to the invention, in general from 0.3 to 3.0 mol, preferably a slight excess, of fluoroalkenyl halide of the formula (III) and, if appropriate, from 0.5 to 2.0 mol, preferably from 0.5 to 1.0 mol, of reaction auxiliary are employed per mole of mercapto derivative of the formula (II). The practice of the reaction and the work-up and isolation of the reaction products are carried out by generally customary processes.

Suitable oxidizing agents for carrying out the process (b) according to the invention are all oxidizing agents which are customarily used for oxidizing sulphur. Particularly suitable are hydrogen peroxide, organic and inorganic peracids, such as, for example, peracetic acid, m-chloroperbenzoic acid, p-nitroperbenzoic acid, magnesium peroxyphthalic acid, potassium peroxymonosulphate or atmospheric oxygen.

Suitable diluents for carrying out the process (b) according to the invention are likewise inert organic solvents. Preference is given to using hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as formic acid, acetic acid or propionic acid, or dipolar aprotic solvents, such as acetonitrile, acetone, ethyl acetate or dimethylformamide; if appropriate also in aqueous solutions.

If appropriate, the process (b) according to the invention can be carried out in the presence of a suitable catalyst. Suitable catalysts are all metal salt catalysts which are usually employed for such sulphur oxidations. Compounds which may be mentioned in an exemplary manner in this context are ammonium molybdate and sodium tungstate.

When carrying out the process (b) according to the invention, the reaction temperatures can be varied within a relatively wide range. In general, the process is carried out at temperatures between −20° C. and +120° C., preferably at temperatures between 0° C. and +100° C.

For carrying out the process (b) according to the invention, in general from 0.8 to 1.2 mol, preferably equimolar amounts, of oxidizing agent are employed per mole of the compound of the formula (Ia) if the oxidation of the sulphur is to be interrupted on the sulphoxide stage. For the oxidation to the sulphone, in general from 1.8 to 3.0 mol, preferably twice the molar amount, of oxidizing agent is employed per mole of the compound of the formula (Ia). The practice of the reaction and work-up and isolation of the end products are carried out by customary processes.

The active compounds having good plant tolerance and favourable warm-blood toxicity are suitable for controlling animal pests, in particular insects, arachnids and nematodes, which are encountered in agriculture, in forestry, in the protection of stored products and of materials, and in the hygiene sector. They may be preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis*.

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The compounds according to the invention can be used with particularly good results for controlling plant-damaging nematodes, such as, for example, againt *Meloidogyne incognita* larvae, for controlling plant-damaging insects, such as, for example, against the peach aphid (*Myzus persicae*), the larvae of the mustard beetle (*Phaedon cochleariae*) and also against the caterpillars of the army worm (*Spodoptera frugiperda*); and also for controlling plant-damaging spider mites (*Tetranychus urticae*).

At appropriate application rates, the compounds according to the invention also have fungicidal properties.

At certain concentrations or application rates, the compounds according to the invention may, if appropriate, also be used as herbicides and microbicides, for example as fungicides, antimycotics and bactericides. If appropriate, they may also be used as intermediates or precursors for the synthesis of further active compounds.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant cultivars protectable or not protectable by plant breeders' rights. Plant parts are to be understood to mean all aboveground and underground parts and organs of plants, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having novel properties ("traits") which can be obtained by conventional breeding, by mutagenesis or by recombinant DNA techniques. This can be varieties, bio- and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred according to the invention include all plants which, in the genetic modification, received genetic material which imparted particularly advantageous useful traits to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from *Bacillus thuringiensis* (for example by the genes CryIA(a), CryIA(b), CryIA (c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexius, elicitous and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still to be developed genetic traits, which plants will be developed and/or marketed in the future.

The plants listed can be treated according to the invention in a particularly advantageous manner with the compounds of the general formula I or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seed, also by applying one or more coats.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:
for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides:
aldimorph, ampropylfos, ampropylfos-potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropane-carboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanato-methyl)-acetamide,
2-phenylphenol (OPP),
3,4-dichloro-1-[4-(difluoromethoxy)-phenyl]-1H-pyrrole-2,5-dione,
3,5-dichloro-N-[cyano-[(1-methyl-2-propynyl)-oxy]-methyl]-benzamide,
3-(1,1-dimethylpropyl)-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophene-dicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulfonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one.
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, Baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., eprinomectin, esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin, IKI 220,
nuclear polyhedrosis viruses,
lambda-cyhalothrin, lufenuron,
malathion, mecarbam, metaldehyde, methamidophos, metharhizium anisopliae, metharhizium flavoviride, methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, selamectin, silafluofen, spinosad, spirodiclofen, sulfotep, sulprofos, S 1812,
tau-fluvalinate, tebufenozide, tebufenpyrad, tebupirimphos, teflubenzuron, tefluthrin, temephos, temivinphos, terbufos, tetrachlorvinphos, thetacypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazurone, trichlophenidine, trichlorfon, triflumuron, trimethacarb, vamidothion, vaniliprole, *Verticillium lecanii*,
YI 5302,
zeta-cypermethrin, zolaprofos,
(1R-cis)-[5-(phenylmethyl)-3-furanyl]-methyl-3-[(dihydro-2-oxo-3(2H)-furanyl-idene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate,
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitro-guanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate.

A mixture with other known active compounds, such as herbicides, or with fertilizers and growth regulators is also possible.

The active compounds according to the invention can furthermore be present when used as insecticides in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

The agents according to the invention are suitable for controlling pathogenic endoparasites encountered in humans and in animal husbandry and livestock breeding, in productive livestock, breeding stock, zoo animals, laboratory animals, animals used in experiments, and pets, and have low toxicity towards warm-blooded animals. They are active against all or some stages of development of the pests and against resistant and normally sensitive species. By controlling the pathogenic endoparasites, it is intended to reduce disease, mortality and decreasing performance (for example in the production of meat, milk, wool, hides, eggs, honey, etc.), so that more economical and simpler animal keeping is possible by using the active compounds. The pathogenic endoparasites include cestodes, trematodes, nematodes and acantocephales, in particular:

From the order of the Pseudophyllidea, for example *Diphyllobothrium* spp., *Spirometra* spp., *Schistocephalus* spp., *Ligula* spp., *Bothridium* spp., *Diphlogonoporus* spp.

From the order of the Cyclophyllidea, for example *Mesocestoides* spp., *Anoplocephala* spp., *Paranoplocephala* spp., *Moniezia* spp., *Thysanosomsa* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

From the subclass of the Monogenea, for example *Gyrodactylus* spp., *Dactylogyrus* spp., *Polystoma* spp.

From the subclass of the Digenea, for example *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

From the order of the Enoplida, for example *Trichuris* spp., *Capillaria* spp., *Trichomosoides* spp., *Trichinella* spp.

From the order of the Rhabditida, for example *Micronema* spp., *Strongyloides* spp.

From the order of the Strongylida, for example *Stronylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Oxyurida, for example *Oxyuris* spp., *Enterobius* spp., *Passalurus* spp., *Syphacia* spp., *Aspiculuris* spp., *Heterakis* spp.

From the order of the Ascaridia, for example *Ascaris* spp., *Toxascaris* spp., *Toxocara* spp., *Parascaris* spp., *Anisakis* spp., *Ascaridia* spp.

From the order of the Spirurida, for example *Gnathostoma* spp., *Physaloptera* spp., *Thelazia* spp., *Gongylonema* spp., *Habronema* spp., *Parabronema* spp., *Draschia* spp., *Dracunculus* spp.

From the order of the Filariida, for example *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

From the order of the Gigantorhynchida, for example *Filicollis* spp., *Moniliformis* spp., *Macracanthorhynchus* spp., *Prosthenorchis* spp.

The livestock and breeding stock include mammals, such as, for example, cattle, horses, sheep, pigs, goats, camels, water buffalo, donkeys, rabbits, fallow deer, reindeer, fur-bearing animals, such as, for example, minks, chinchilla or racoon, birds, such as, for example, chickens, geese, turkeys, ducks or ostriches, freshwater fish and sea fish, such as, for example, trout, carp and eels, reptiles and insects, such as, for example, honey bee and silkworm.

The laboratory and test animals include mice, rats, guinea pigs, golden hamsters, dogs and cats.

The pets include dogs and cats.

Administration can be effected prophylactically as well as therapeutically.

The active substances are administered, either directly or in the form of suitable preparations, enterally, parenterally, dermally, nasally, by treating the habitat or with the aid of shaped articles containing the active compound, such as, for example, strips, plates, tapes, collars, ear tags, limb bands or marking devices.

Enteral administration of the active compounds is effected for example orally in the form of powders, tablets, capsules, pastes, drinks, granules, solutions, suspensions and emulsions which can be applied orally, boluses, medicated feed or drinking water. Dermal application is effected, for example, in the form of dipping, spraying, or pouring-on and spotting-on. Parenteral administration is effected, for example, in the form of injection (intramuscular, subcutaneous, intravenous or intraperitoneal) or by implants.

Suitable preparations include:

Solutions, such as solutions for injection, oral solutions, concentrates for oral administration after dilution, solutions for use on the skin or in body cavities, pour-on formulations, gels;

Emulsions and suspension for oral or dermal administration and for injection; semi-solid preparations;

Formulations in which the active compound is incorporated in an ointment base or in an oil-in-water or water-in-oil emulsion base;

Solid preparations, such as powders, premixes or concentrates, granules, pellets, tablets, boluses, capsules; aerosols and inhalants, shaped articles containing the active compound.

Solutions for injection are administered intravenously, intramuscularly and subcutaneously. Solutions for injection are prepared by dissolving the active compound in a suitable solvent and, if desired, adding additives, such as solubilizers, acids, bases, buffer salts, antioxidants, or preservatives. The solutions are sterile-filtered and decanted into containers.

Suitable solvents include: physiologically acceptable solvents, such as water, alcohols, such as ethanol, butanol, benzyl acohol, glycerol, propylene glycol, polyethylene glycols and N-methyl-pyrrolidone, and their mixtures.

If appropriate, the active compounds can also be dissolved in physiologically acceptable vegetable or synthetic oils which are suitable for injection.

Suitable solubilizers include: solvents which facilitate the dissolution of the active compound in the main solvent or which prevent precipitation of the active compound. Examples of solubilizers are polyvinylpyrrolidone, polyethoxylated castor oil and polyethoxylated sorbitan esters.

The following are preservatives: benzyl alcohol, trichlorobutanol, p-hydroxybenzoic esters or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on. These solutions are prepared as described above in the case of the solutions for injection.

It may be advantageous to add thickeners in the preparation process. The following are thickeners: inorganic thickeners, such as bentonites, colloidal silica, aluminium monostearate, or organic thickeners, such as cellulose derivatives, polyvinyl alcohols and their copolymers, acrylates and methacrylates.

Gels are applied to the skin or smoothed on or introduced into body cavities. Gels are prepared by adding such an amount of thickener to solutions which have been prepared as described for the solutions for injection that a clear composition is formed which has an ointment-like consistency. The thickeners used are the thickeners indicated further above.

Pour-on and spot-on formulations are poured or splashed onto limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other auxiliaries, such as colorants, absorption promoters, antioxidants, photostabilizers or tackifiers are added.

Suitable solvents include: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethylacetamide, N-methylpyrrolidone, or 2,2-dimethyl-4-oxymethylene-1,3-dioxolane.

Colorants are all colorants which can be dissolved or suspended and which are approved for use in animals.

Examples of absorption promoters are DMSO, spreading oils, such as isopropyl myristate, dipropylene glycol pelargonate, silicone oils, fatty acid esters, triglycerides or fatty alcohols.

The following are antioxidants: sulfites or metabisulfites, such as potassium metabisulfite, ascorbic acid, butylhydroxytoluene, butylhydroxyanisole or tocopherol.

Example of photostabilizers are novantisolic acid.

Tackifiers are, for example, cellulose derivatives, starch derivatives, polyacrylates or natural polymers such as alginates or gelatin.

Emulsions can be administered orally, dermally or as injections.

Emulsions are either the water-in-oil type or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colorants, absorption promoters, preservatives, antioxidants, photostabilizers, and viscosity-increasing substances.

Suitable hydrophobic phases (oils) include: paraffin oils, silicone oils, natural vegetable oils such as sesame seed oil, almond oil or castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyryl adipate, hexyl laurate, dipropylene glycol pelargonate, esters of a branched fatty acid having a medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial duck uropygial fat, dibutyl phthalate, diisopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

Suitable hydrophilic phases include:
water, alcohols, such as, for example, propylene glycol, glycerol, sorbitol and their mixtures.

Suitable emulsifiers include: nonionic surfactants, for example polyethoxylated castor oil, polyethoxylated sorbitan monooleate, sorbitan monostearate, glycerol monostearate, polyoxyethyl stearate or alkylphenol polyglycol ethers;

Ampholytic surfactants, such as disodium N-lauryl-β-iminodipropionate or lecithin;

Anionic surfactants, such as Na lauryl sulfate, fatty alcohol ether sulfates, and the monoethanolamine salt of mono/dialkylpolyglycol ether orthophosphoric ester;

Cation-active surfactants such as cetyltrimethylammonium chloride.

Suitable other auxiliaries include: substances which increase the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colorants, absorption promoters, preservatives, antioxidants and photostabilizers.

Suitable liquid excipients include all homogeneous solvents and solvent mixtures.

Suitable wetting agents (dispersants) include the surfactants indicated further above.

Suitable other auxiliaries include those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Suitable excipients include all physiologically acceptable solid inert substances. Suitable for this purpose are inorganic and organic substances. Inorganic substances are, for example, common salt, carbonates, such as calcium carbonate, hydrogen carbonates, aluminium oxides, silicas, clays, precipitated or colloidal silica, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colorants which have already been mentioned further above.

Other suitable auxiliaries are lubricants and glidants, such as, for example, magnesium stearate, stearic acid, talc, bentonites, disintegrants, such as starch or crosslinked polyvinylpyrrolidone, binders, such as, for example, starch, gelatin or linear polyvinylpyrrolidone, and dry binders, such as microcrystalline cellulose.

In the preparations, the active compounds can also be present in mixtures with synergists or other active compounds which are active against pathogenic endoparasites. Examples of such active compounds are L-2,3,5,6-tetrahydro-6-phenyl-imidazothiazole, benzimidazole carbamates or pyrantel.

Ready-to-use preparations contain the active compounds in concentrations of 10 ppm to 20 percent by weight, preferably from 0.1 to 10 percent by weight.

Preparations which are diluted before use contain the active compounds in concentrations of 0.5 to 90 percent by weight, preferably from 5 to 50 percent by weight.

In general it has been found to be advantageous to administer the mixture according to the invention in amounts of from about 10 to about 100 mg of active compound per kg of body weight per day to obtain good results. Preference is given to using from 10 to 50 mg of active compound mixture per kg of body weight.

In the compositions, the weight ratio of praziquantel and/or epsiprantel to depsipeptide is generally 1:1–10, preferably 1:1–2 and very particularly preferably 1:1.

It has furthermore been found that the compounds according to the invention also have a strong insecticidal action against insects which destroy industrial materials.

The following insects may be mentioned as examples and as being preferred—but without any limitation:

Beetles, such as
*Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec.,
*Apate monachus, Bostrychus capucins, Heterobostrychus brunneus, Sinoxylon* spec. and *Dinoderus minutus.*

Hymenopterons, such as
*Sirex juvencus, Urocerus gigas, Urocerus gigas taignus* and *Urocerus augur.*

Termites, such as
*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials in the present context are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising this are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyes and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by a polar organic chemical solvent or solvent mixture. Organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octylisothiazolin-3-one and 4,5-dichloro-N-octylisothiazolin-3-one.

The compounds according to the invention can at the same time be employed for protecting objects which come into contact with salt water or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis-(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl (bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Aviculariidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

PREPARATION EXAMPLES

Example 1

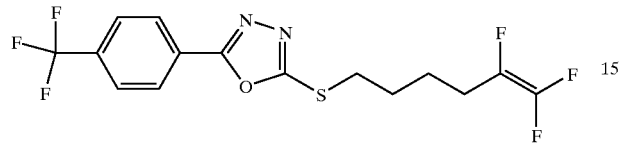

(Process a)

4.7 g (34 mmol) of potassium carbonate and then 2.7 g (12.7 mmol) of 6,6,5-trifluorohex-5-enyl bromide are added to a solution of 2.8 g (11.4 mmol) of 2-mercapto-5-(4-trifluoromethylphenyl)-1,3,4-oxadiazole in 30 ml of acetonitrile. The reaction mixture is heated at reflux for 6 hours and then poured into water and extracted with dichloromethane. Removal of the solvent gives 4.7 g of crude product which are purified on silica gel using the system dichloromethane/ethyl acetate (4:1).

This gives 3.2 g (73.4% of theory) of 2-(6,6,5-trifluorohex-5-enylthio)-5-(4-trifluoromethyl-phenyl)-1,3,4-oxadiazole of melting point 40° C.

The compounds of formula (I) listed in Tables 1 and 2 below are obtained similarly to Example 1 and/or in accordance with the general statements on the preparation:

TABLE 1

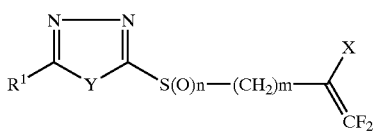

(IB)

| Ex. No. | R$^1$ | Y | n | m | X | logP (pH2) or NMR |
|---|---|---|---|---|---|---|
| 2 | 4-F$_3$C-phenyl | O | 0 | 4 | H | 4.77 |
| 3 | phenyl | O | 0 | 4 | F | 3.97 |
| 4 | phenyl | O | 0 | 4 | H | 4.08 |
| 5 | CH$_3$S— | S | 0 | 4 | F | 3.69 |
| 6 | CH$_3$S— | S | 0 | 4 | H | 3.79 |
| 7 | 2-thienyl | O | 0 | 4 | F | 3.74 |
| 8 | 2-thienyl | O | 0 | 4 | H | 3.84 |
| 9 | CH$_3$S(O)— | S | 0 | 4 | F | 2.46 |
| 10 | CF$_3$— | S | 0 | 4 | H | 4.32 |
| 11 | CF$_3$— | S | 0 | 4 | F | 4.21 |
| 12 | (CH$_3$)$_2$CH(CH$_2$)$_2$S— | S | 0 | 4 | H | 5.68 |
| 13 | (CH$_3$)$_2$CH(CH$_2$)$_2$S— | S | 0 | 4 | F | 5.53 |
| 14 | 5-(F$_3$C)-pyridin-2-yl | O | 0 | 4 | F | 3.90 |
| 15 | 4-Cl-phenyl | O | 0 | 4 | F | 4.55 |
| 16 | 2,6-dichloropyridin-4-yl | O | 0 | 4 | F | 4.55 |
| 17 | ClCH$_2$CH$_2$S— | S | 0 | 4 | F | 4.28 |
| 18 | 5-(F$_3$C)-pyridin-2-yl | S | 0 | 4 | F | 4.95 |
| 19 | 4-Cl-phenyl | S | 0 | 4 | F | 5.05 |
| 20 | HS— | S | 0 | 4 | F | $^1$H-NMR in CDCl$_3$/ δ in ppm: 3.3(2H); 2.35(2H); 1.75(2H) |
| 21 | CF$_2$=CF—(CH$_2$)$_4$—S— | S | 0 | 4 | F | 5.27 |
| 22 | 4-Cl-phenyl | O | 0 | 4 | H | 4.68 |
| 23 | ClCH$_2$CH$_2$S— | S | 0 | 4 | H | 4.40 |
| 24 | C$_2$H$_5$O— | S | 0 | 4 | F | 3.80 |
| 25 | i-C$_3$H$_7$O— | S | 0 | 4 | F | 4.24 |
| 26 | 4-Cl-phenyl | S | 0 | 4 | H | 5.19 |

TABLE 1-continued (IB)

$$R^1-Y\underset{N=N}{\overset{}{\diagdown}}S(O)n-(CH_2)m-\overset{X}{\underset{CF_2}{=}}$$

| Ex. No. | R¹ | Y | n | m | X | logP (pH2) or NMR |
|---|---|---|---|---|---|---|
| 27 | F₂C=CF—(CH₂)₂—S— | S | O | 4 | F | 4.71 |
| 28 | F₂C=CF—(CH₂)₂—S— | S | O | 4 | H | 4.84 |
| 29 | F₂CH—S— | S | O | 4 | F | 3.82 |
| 30 | F₂CH—S— | S | O | 4 | H | 3.91 |

TABLE 2

(IC)

$$R^2\underset{S}{\overset{N}{\diagdown}}S(O)n-(CH_2)m-\overset{X}{\underset{CF_2}{=}}$$

| Ex. No. | R² | n | m | X | logP (pH 2) |
|---|---|---|---|---|---|
| IB-1 | H | O | 4 | H | 1.48 |
| IB-2 | H | O | 4 | F | 1.51 |

The logP values were determined in accordance with EEC Directive 79/831 Annex V.A8 by HPLC (gradient method, acetonitrile/0.1% aqueous phosphoric acid).

Example A

Meloidogyne Test

| Solvent: | 30 parts by weight of dimethylformamide or 4 parts by weight of acetone |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Containers are filled with sand, solution of active compound, Meloidogyne incognita egg/larvae suspension and lettuce seeds. The lettuce seeds germinate and the plants develop. On the roots, galls are formed.

After the desired period of time, the nematicidal action is determined in % using gall formation as a measure. 100% means that no galls were found; 0% means that the number of galls on the treated plants corresponds to that of the untreated control.

In this test, for example, at an exemplary active compound concentration of 20 ppm, the compounds of Preparation Examples 2, 4, 5, 7, 8, 12, 13, 14, 15 and 19 exhibit an activity of 100% and the compound of Preparation Example 18 exhibits an activity of 90%, in each case after 14 days.

Example B

Myzus Test

| Solvent: | 30 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with emulsifier-containing water to the desired concentrations.

Broad bean (Vicia faba) seedlings which are infested by the peach aphid (Myzus persicae) are dipped into the preparation of active compound of the desired concentration and put into a plastic box.

After the desired period of time, the kill in % is determined. 100% means that all animals have been killed; 0% means that none of the animals have been killed.

In this test, for example, at an exemplary active compound concentration of 10 ppm, the compounds of Preparation Examples 2 and 6 effect a kill of 95%, the compound of Preparation Example 7 a kill of 89% and the compounds of Preparation Examples 8 and 10 a kill of 100%, in each case after 6 days.

Example C

Phaedon Larvae Test

| Solvent: | 30 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (Brassica oleracea) are treated by being dipped into the preparation of active compound of the desired concentration and are populated with larvae of the mustard beetle (Phaedon cochleariae) while the leaves are still moist.

After the desired period of time, the kill in % is determined. 1000 ppm means that all beetle larvae have been killed; 0% means that none of the beetle larvae have been killed.

In this test, for example, at an exemplary active compound concentration of 1000 ppm, the compounds of Preparation Examples 2, 4, 6, 11, 12, 15, 18 and 19 effect a kill of 100% after 7 days.

Example D

Spodoptera frugiperda Test

| Solvent: | 30 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (Brassica oleracea) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test, for example, at an exemplary active compound concentration of 1000 ppm, the compounds of Preparation Examples 1 and 10 effect a kill of 100% after 7 days.

Example E
Tetranychus Test (OP-resistant/Dip Treatment)

| Solvent: | 30 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the kill in % is determined. 100% means that all spider mites have been killed; 0% means that none of the spider mites have been killed.

In this test, for example, at an exemplary active compound concentration of 0.1%, the compound of Preparation Example 6 effects a kill of 98% and the compounds of Preparation Examples 2, 4, 8 and 12 effect a kill of 98%, in each case after 7 days.

Example F
Test with *Boophilus microplus* Resistant (SP-resistant Parkhurst Strain/I)

| Test animals: | adult females which have sucked themselves full |
|---|---|
| Solvent: | dimethyl sulphoxide |

20 mg of active compound are dissolved in 1 ml of dimethyl sulphoxide, more dilute concentrations are prepared by dilution with distilled water.

10 adult *Boophilus microplus* res. are dipped for 1 minute into the preparation of active compound to be tested. The animals are transferred into plastic beakers and kept in a climatized room, and the kill rate is then determined.

100% means that all tics have been killed; 0% means that none of the tics have been killed.

In this test, for example, at an exemplary active compound concentration of 100 ppm, the compounds of Preparation Examples 6, 10 and 12 each effect a kill of 100%.

Example G
Test with *Boophilus microplus* Resistant (SP-resistant Parkhurst Strain/II)

| Test animals: | adult females which have sucked themselves full |
|---|---|
| Solvent: | dimethyl sulphoxide |

20 mg of active compound are dissolved in 1 ml of dimethyl sulphoxide, more dilute concentrations are prepared by dilution in the same solvent.

The test is carried out in 5 replications. 1 $\mu$l of the solutions is injected into the abdomen, and the animals are transferred into dishes and kept in a climatized room. After 7 days, the activity is checked by examination for oviposition of fertile eggs. Eggs whose fertility is not visible from the outside are stored in glass tubes in a controlled-environment cabinet until the larvae have hatched. An activity of 100% means that no tick has produced any fertile eggs.

In this test, for example, at an exemplary amount of active compound of 20 $\mu$g per animal, the compounds of Preparation Examples 2, 5, 6, 8, 10, 12, 17 and 21 each effect a kill of 100%. At an amount of active compound of 4 and 0.8 $\mu$g per animal, for example, the compounds of Preparation Examples 6, 8, 10, 12, 17 and 21 each exhibit an activity of 100%.

Example H
Blowfly Larvae Test/Development-inhibitory Action

| Test animals: | *Lucilia cuprina* larvae |
|---|---|
| Solvent: | dimethyl sulphoxide |

20 mg of active compound are dissolved in 1 ml of dimethyl sulphoxide, more dilute concentrations are prepared by dilution with distilled water.

About 20 *Lucilia cuprina* larvae are introduced into a test tube which contains about 1 cm$^3$ of horse meat and 0.5 ml of the preparation of active compound to be tested. After 24 hours and 48 hours, the efficacy of the preparation of active compound is determined. The test tubes are transferred into a beaker whose bottom is covered with sand. After a further 2 days, the test tubes are removed and the pupae are counted.

The efficacy of the preparation of active compound is assessed by the number of flies that have hatched after 1.5 times the period of development of an untreated control. 100% means that no flies have hatched; 0% means that all flies have hatched normally.

In this test, at an exemplary active compound concentration of 100 ppm, the compounds of Preparation Examples 8 and 12 effect a kill of 100%.

Example J
Cockroach Test

| Test animals: | *Blatella germanica* or *Periplaneta americana* |
|---|---|
| Solvent: | dimethyl sulphoxide |

20 mg of active compound are dissolved in 1 ml of dimethyl sulphoxide, more dilute concentrations are prepared by dilution with distilled H$_2$O.

4 test animals are dipped for 1 minute into the preparation of active compound to be tested.

The test animals are transferred into plastic beakers and kept in a climatized room for 7 days, after which the kill rate is determined.

100% means that all cockroaches have been killed, 0% means that none of the cockroaches have been killed.

In this test, at an exemplary active compound concentration of 100 ppm, the compounds of Preparation Examples 8 and 10 each effect a kill of 100%, the compound of Preparation Example 6 effects a kill of 75%.

Example K

Test with Cat Fleas/Oral Uptake

| Test animals: | adults of Ctenocephalides felis |
|---|---|
| Solvent: | dimethyl sulphoxide (DMSO) |

To produce a suitable formulation, a suitable solution of active compound is prepared from 20 mg of active compound and 1 ml of DMSO. 15 µl of this formulation are added to 3 ml of citrated cattle blood and stirred.

10 unfed adult fleas (*Ctenocephalides felis*, strain "Georgi") are placed into a chamber (Ø 3.2 cm) whose top and bottom are closed with gauze. A metal cylinder whose underside is covered with parafilm is placed onto the chamber. The cylinder contains 3 ml of blood/active compound formulation which can be taken up by the fleas through the parafilm membrane. Whereas the blood is warmed to 37° C., the temperature in the area of the flea chambers is adjusted to 25° C. Controls are mixed with the same volume of DMSO, without addition of a compound. The determinations are carried out in triplicate.

After 28 h, the mortality in % (=dead fleas) is determined.

Compounds which effect an at least 25% kill of the fleas within 28 h are judged to be effective.

In this test, at an exemplary active compound concentration of 100 ppm, the compounds of Preparation Examples 2, 6, 8, 10, 12 and 15 effected a kill of 93, 81, 72, 87, 94 and 57%, respectively.

Example L

*Nippostrongylus brasiliensis* In-vitro

| Test animals: | adult *Nippostrongylus brasiliensis* |
|---|---|
| Solvent: | dimethyl suiphoxide |

*Nippostrongylus brasiliensis* worms are isolated from the small intestine of female Wistar rats and collected in aqueous 0.9% NaCl containing 20 µg of sisomycin/ml and 2 µg of Canesten/ml. The incubation of the two groups of worms (of male/female sex) is carried out in 1.0 ml of medium, which is used for determining the acetylcholinesterase activity. Incubation conditions and the determination of the enzyme activity are described in Martin et al., Pesticide Science (1996) 48, 343–349. The compounds are dissolved in the stated solvent (10 mg per 0.5 ml) and diluted to the desired concentration. The controls contain only the solvent.

The vitality of the worms is characterized by the acetylcholinesterase activity which the worms have secreted actively into the incubation medium. The acetylcholinesterase acivity is classified in accordance with the abovementioned work by Martin et al. (1996). 0 means no activity, 1 means weak activity, 2 means good activity and 3 means full activity (<50%, 50–75%, >75%, 100% enzyme inhibition).

In this test, for example, at an exemplary active compound concentration of 10 ppm, the compounds of Preparation Examples 6, 12 and 17 show weak activity; the compounds of Preparation Examples 5 and 8 show good activity. At an exemplary active compound concentration of 100 ppm, for example, the compounds of Preparation Examples 2 and 21 show weak activity, and the compounds of Preparation Examples 6, 12 and 17 show good activity.

Example M

*Trichinella spiralis* In-vitro

| Test animals: | *Trichinella spiralis* larvae |
|---|---|
| Solvent: | dimethyl suiphoxide |

*Trichinella spiralis* larvae are isolated from skeletal muscles and subcutaneous muscles of SPF/CFW1 mice and collected in aqueous 0.9% NaCl containing 20 µg of sisomycin/ml. Per determination, 20 larvae are incubated in 2 ml of a nutrient solution (20 g of Bacto Casitone/l, 10 g of yeast extract/l, 5 g of glucose/l, 0.8 g of $KH_2PO_4$/l, 0.8 g of $K_2HPO_4$; 10 g of sisomycin/ml and 1 µg of Canesten/ml; pH=7.2).

The incubation and the determination have been described in Martin et al., Pesticide Science (1996) 48, 343–349. 10 mg of the test compound are dissolved in 0.5 ml of the stated solvent, and such an amount of the resulting solution is added to the incubation medium that the desired concentration is reached. The controls contain only the solvent.

After an incubation time of 5 days at a temperature of 19° C., the experiment is terminated. The anthelmintic activity of a substance is categorized into 4 stages. 0 means no activity, 1 means weak activity, 2 means good activity and 3 means full activity (<50%, 50–75%, >75%, 100% of the larvae dead).

In this test, for example, at an exemplary active compound concentration of 10 ppm, the compounds of Preparation Examples 5 and 8 show good activity. At an exemplary active compound concentration of 100 ppm, for example, the compound of Preparation Example 6 shows good activity. At an exemplary active compound concentration of 100 ppm, the compounds of Preparation Examples 2, 10, 12, 17 and 21 show no activity in this test.

What is claimed is:

1. A compound of the formula (I)

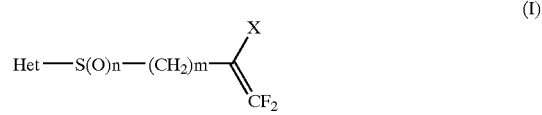

(I)

in which

X represents hydrogen, halogen, or alkyl, m represents an integer from 3 to 10, n represents 0, 1, or 2, and Het represents a group

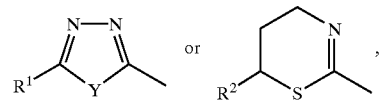

where

R¹ represents hydrogen; mercapto; optionally halogen-substituted alkyl, alkoxy, alkylthio, alkylsulphinyl, alkylsulphonyl, or alkenyl; optionally substituted aryl; or optionally substituted heterocyclyl, Y represents oxygen or sulphur, and R² represents hydrogen; alkyl; or optionally substituted aryl.

2. A process for preparing a compound of the formula (I) according to claim 1 comprising (a) reacting a mercapto derivative of the formula (II)

in which Het is as defined for formula (I) of claim 1, or a salt thereof, with a fluoroalkenyl halide of the formula (III)

in which
X and m are each as defined for formula (I) of claim 1, and
Hal represents halogen,
in the presence of a diluent and optionally in the presence of a basic reaction auxiliary,
to form a heterocyclic fluoroalkenyl thioether of the formula (IA)

in which Het, X, and m are each as defined for formula (I) of claim 1, and (b) for preparing a compound of formula (I) in which n is 1 or 2, oxidizing the heterocyclic fluoroalkenyl thioether of the formula (IA) with an oxidizing agent, optionally in the presence of a diluent and optionally in the presence of a catalyst.

3. A compound of the formula (I) according to claim 1 in which
X represents hydrogen, fluorine, chlorine, bromine, or $C_1$–$C_4$-alkyl,
m represents an integer from 3 to 8,
n represents 0 or 2, and
Het represents a group

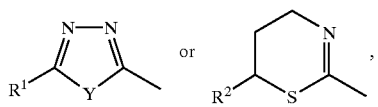

where
$R^1$ represents hydrogen; mercapto; $C_1$–$C_8$-alkyl, $C_1$–$C_8$-alkoxy, $C_1$–$C_8$-alkylthio, $C_1$–$C_8$-alkylsulphinyl, $C_1$–$C_8$-alkylsulphonyl, or $C_2$–$C_8$-alkenyl, each of which is optionally mono- or polysubstituted by identical or different halogens; phenyl that is optionally mono- to pentasubstituted by identical or different substituents selected from the group consisting of halogen, nitro, cyano, thiocyanato, and $C_1$–$C_4$-alkyl, $C_1$–$C_4$-alkoxy, or $C_1$–$C_4$-alkylthio, each of which $C_1$–$C_4$-alkyl, $C_1$–$C_4$-alkoxy, or $C_1$–$C_4$-alkylthio is optionally mono- or polysubstituted by identical or different halogens; or 5- or 6-membered heterocyclyl having 1 to 3 N, O or S heteroatoms and that is optionally mono- to pentasubstituted by identical or different substituents selected from the group consisting of halogen, nitro, cyano, thiocyanato, and $C_1$–$C_4$-alkyl, $C_1$–$C_4$-alkoxy, or $C_1$–$C_4$-alkylthio, each of which $C_1$–$C_4$-alkyl, $C_1$–$C_4$-alkoxy, or $C_1$–$C_4$-alkylthio is optionally mono- or polysubstituted by identical or different halogens,
Y represents oxygen or sulphur, and
$R^2$ represents hydrogen or $C_1$–$C_4$-alkyl.

4. A compound of the formula (I) according to claim 1 in which
X represents hydrogen or fluorine,
m represents integers from 3 to 6,
n represents 0, and
Het represents a group

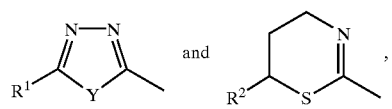

where
$R^1$ represents hydrogen; sulphur; $C_1$–$C_6$-alkyl, $C_1$–$C_6$-alkoxy, $C_1$–$C_6$-alkylthio, $C_1$–$C_6$-alkylsulphinyl, $C_1$–$C_6$-alkylsulphonyl, or $C_2$–$C_6$-alkenyl, each of which is optionally mono- to pentasubstituted by identical or different substituents selected from the group consisting of fluorine and chlorine; phenyl that is optionally mono- to trisubstituted by identical or different substituents selected from the group consisting of fluorine, chlorine, bromine, nitro, cyano, thiocyanato, and $C_1$–$C_4$-alkyl, $C_1$–$C_4$-alkoxy, or $C_1$–$C_4$-alkylthio, each of which $C_1$–$C_4$-alkyl, $C_1$–$C_4$-alkoxy, or $C_1$–$C_4$-alkylthio is optionally mono- to pentasubstituted by identical or different substituents selected from the group consisting of fluorine and chlorine; or furyl, thienyl, pyrazolyl, pyridinyl, or pyrimidinyl, each of which is optionally mono- to trisubstituted by identical or different substituents selected from the group consisting of fluorine, chlorine, bromine, nitro, cyano, thiocyanato, and $C_1$–$C_4$-alkyl, $C_1$–$C_4$-alkoxy, or $C_1$–$C_4$-alkylthio, each of which $C_1$–$C_4$-alkyl, $C_1$–$C_4$-alkoxy, or $C_1$–$C_4$-alkylthio is optionally mono- to pentasubstituted by identical or different substituents selected from the group consisting of fluorine and chlorine,
Y represents oxygen or sulphur, and
$R^2$ represents hydrogen or $C_1$–$C_4$-alkyl.

5. A compound of the formula (I) according to claim 1 in which
m represents 4, and
Het represents a group

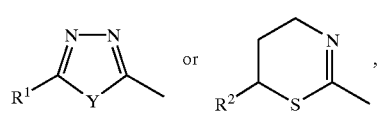

where
$R^1$ represents hydrogen; mercapto; methyl, ethyl, n- or i-propyl, n-, i-, s-, or t-butyl, n-, i-, or neo-pentyl, methoxy, ethoxy, n- or i-propoxy, n-, i-, s-, or t-butoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, each of which is optionally mono- to pentasubstituted by identical or different substituents selected from the group consisting of fluorine and chlorine; ethenyl, propenyl, butenyl, pentenyl, or hexenyl; ethenylthio, propenylthio, butenylthio, pentenylthio, or hexenylthio; ethylsulphinyl, propenylsulphinyl, butenylsulphinyl, pentenylsulphinyl, or hexenylsulphinyl; ethenylsulphonyl, propenylsulphonyl, butenylsulphonyl, pentenylsulphonyl, or hexenylsulphonyl; phenyl that is optionally mono- or disubstituted by identical or different substituents selected from the group consisting of fluorine, chlorine, nitro, cyano, thiocyanato, and methyl, ethyl, methoxy, ethoxy, methylthio, or ethylthio, each of which methyl, ethyl, methoxy, ethoxy, methylthio, or ethylthio is optionally mono- to pentasubstituted by identical or different substituents selected from the group consisting of fluorine and chlorine; or thienyl or pyridinyl, each of which is optionally mono- or disubstituted by identical or different substituents selected from the group consisting of fluorine, chlorine, nitro, cyano, thiocyanato, and methyl, ethyl, methoxy, ethoxy, methylthio, or ethylthio, each of which methyl, ethyl, methoxy, ethoxy, methylthio, or ethylthio is optionally mono- to pentasubstituted by identical or different substituents selected from the group consisting of fluorine and chlorine, Y represents oxygen or sulphur, and $R^2$ represents hydrogen, methyl, ethyl, or n- or i-propyl.

6. A compound of the formula (I) according to claim 1 in which Het represents the group

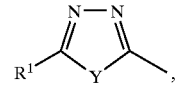

where $R^1$ and Y are each as defined for formula (I) of claim 1.

7. A pesticide comprising a pesticidally effective amount of one or more compounds of the formula (I) according to claim 1 and customary extenders.

8. A method for controlling pests comprising allowing one or more compounds of the formula (I) according to claim 1 to act on pests and/or their habitat.

9. A method for controlling pests comprising allowing a pesticide according to claim 7 to act on pests and/or their habitat.

10. A process for preparing pesticides comprising mixing a compound of the formula (I) according to claim 1 with extenders and/or surfactants.

* * * * *